US012544552B1

(12) United States Patent
Hochareon et al.

(10) Patent No.: US 12,544,552 B1
(45) Date of Patent: Feb. 10, 2026

(54) THERAPY DELIVERY SYSTEM

(71) Applicant: NirvaMed, Inc., Bloomington, MN (US)

(72) Inventors: Pramote Hochareon, Vadnais Heights, MN (US); Cynthia Clague, Minnetonka, MN (US); Cattleya Ounekeo, Bloomington, MN (US); Panapat Uawithya, Bangkok (TH); Troy Ziegler, Apple Valley, MN (US); Don Evans, Saint Paul, MN (US)

(73) Assignee: NirvaMed, Inc., Bloomington, MN (US)

( * ) Notice: Subject to any disclaimer, the term of this patent is extended or adjusted under 35 U.S.C. 154(b) by 466 days.

(21) Appl. No.: 18/116,610

(22) Filed: Mar. 2, 2023

Related U.S. Application Data

(60) Provisional application No. 63/316,056, filed on Mar. 3, 2022.

(51) Int. Cl.
*A61M 60/205* (2021.01)
*A61M 60/148* (2021.01)
*A61M 60/50* (2021.01)

(52) U.S. Cl.
CPC ... *A61M 60/148* (2021.01); *A61M 2205/3334* (2013.01)

(58) Field of Classification Search
CPC .......... A61M 2205/3334; A61M 60/13; A61M 60/135; A61M 60/148; A61M 60/17; A61M 60/205; A61M 60/237; A61M 60/414; A61M 60/50; A61M 60/508; A61M 60/81; A61M 60/818; A61M 60/824; A61M 60/829; A61M 60/857
See application file for complete search history.

(56) References Cited

U.S. PATENT DOCUMENTS

| | | | |
|---|---|---|---|
| 4,714,460 | A | 12/1987 | Calderon |
| 4,867,742 | A | 9/1989 | Calderon |
| 5,385,548 | A | 1/1995 | Williams et al. |
| 5,411,479 | A | 5/1995 | Bodden |
| 5,533,957 | A | 7/1996 | Aldea |
| 5,597,377 | A | 1/1997 | Aldea |
| 5,662,606 | A | 9/1997 | Huybregts |
| 5,794,629 | A | 8/1998 | Frazee |
| 5,817,046 | A | 10/1998 | Glickman |
| 5,865,789 | A | 2/1999 | Hattler |
| 6,186,146 | B1 | 2/2001 | Glickman |
| 6,287,273 | B1 | 9/2001 | Allers |
| 6,336,910 | B1 | 1/2002 | Ohta et al. |

(Continued)

FOREIGN PATENT DOCUMENTS

WO PCT/SE2003/000284 8/2003

OTHER PUBLICATIONS

Search Report issued Feb. 2, 2016 in European Patent Application serial No. 11740297.4.

*Primary Examiner* — Jon Eric C Morales
(74) *Attorney, Agent, or Firm* — Billion & Armitage

(57) ABSTRACT

A therapy delivery system for delivering therapy to a target region in a body includes an inflow channel and an outflow channel through which regulated inflow and inflow may be conveyed. The inflow and outflow is controlled by flow regulators in a manner to deliver a therapeutic agent to the target region and achieve a therapeutic response. A controller dynamically adjusts a ratio of inflow to outflow in response to an input that is related to changing physiological conditions.

16 Claims, 6 Drawing Sheets

(56) References Cited

U.S. PATENT DOCUMENTS

| | | | |
|---|---|---|---|
| 6,386,202 | B1 | 5/2002 | Frazee |
| 6,626,857 | B1 | 9/2003 | Ohta |
| 6,682,499 | B2 | 1/2004 | Lenker |
| 6,699,231 | B1 | 3/2004 | Sternman et al. |
| 6,821,263 | B2 | 11/2004 | Lenker |
| 6,896,663 | B2 | 5/2005 | Barbut |
| 7,347,810 | B2 | 3/2008 | Stamos |
| 2002/0077581 | A1 | 6/2002 | Davidner |
| 2002/0128586 | A1 | 9/2002 | Barbut |
| 2003/0212304 | A1 | 11/2003 | Lattouf |
| 2004/0034272 | A1 | 2/2004 | Diaz |
| 2006/0149219 | A1 | 7/2006 | Calderon |
| 2006/0149393 | A1 | 7/2006 | Calderon |
| 2006/0167398 | A1 | 7/2006 | Solar |
| 2006/0258980 | A1 | 11/2006 | Bridges |
| 2008/0041516 | A1 | 2/2008 | Chiu et al. |

THERAPY DELIVERY SYSTEM

CROSS-REFERENCE TO RELATED APPLICATIONS

This application claims priority to U.S. Provisional Patent Application Ser. No. 63/316,056, filed on Mar. 3, 2022 and entitled "Therapy Delivery System", the content of which being incorporated herein in its entirety.

FIELD OF THE INVENTION

The present invention relates to perfusion of body tissues, and more particularly to a system for delivering therapeutic perfusion inflow to a targeted body region, tissue, or organ, and for controlling outflow from the targeted body region, tissue, or organ in a manner that maximizes the therapeutic benefit of the perfusion while minimizing potentially negative side effects of the perfusion treatment.

BACKGROUND OF THE INVENTION

Therapy delivery techniques have typically relied upon systemic circulation, accessed via oral, intravenous, intramuscular, percutaneous, subdermal, and inhalation routes. Local treatment with the therapy may be inefficient or ineffective as a result of the systemic administration. Moreover, detrimental side effects of the intended therapy may be encountered as a result of the systemic delivery.

An aspirational application for localized therapy delivery is the treatment of ischemic tissue caused by an acute severe disruption in arterial circulation to the damaged tissue. Examples of ischemic injuries are myocardial infarction (heart attack) and cerebrovascular accident (stroke). Treatment of ischemic injury has typically involved a direct arterial intervention. However, conventional arterial intervention techniques require significant time to complete, and introduce risk of secondary injury, such as through arterial emboli and reperfusion injury, which may be caused by a sudden return of blood supply to the tissue after the arterial disruption is resolved.

Percutaneous coronary intervention (PCI), such as stent and/or balloon angioplasty and/or thrombolytic therapy is a known treatment that seeks to re-establish the tissue perfusion to the myocardium as early as possible in order to minimize tissue damage, and to promote tissue salvage. PCI, however, can cause clot debris to flow downstream and result in a distal occlusion of smaller arteries.

Retrograde therapeutic perfusion, such as perfusion of oxygenated blood delivered retrogradely to the endangered ischemic myocardium, has been explored as a stand-alone or adjunctive treatment to PCI to cause oxygenated blood to rapidly reach an underperfused myocardium tissue. Retroperfusion of oxygenated blood has also been explored in the context of ischemic brain stroke, in which autologous oxygenated blood may be pumped into one or both of the cerebral venous sinuses through the jugular veins.

In addition to rapidly providing oxygenated blood to ischemic tissue, venous retroperfusion may provide an advantageous technique for therapeutic hypothermia of retroperfused tissue. Mild hypothermia (32-33° C.) with reperfusion therapy has been shown to provide a significant improvement of tissue protection when compared to reperfusion therapy alone. By directly treating tissue structures with therapeutic cooling, many undesirable effects of systemic cooling may be avoided.

An example system for local therapy delivery, including localized perfusion therapy, is described in U.S. Pat. No. 11,173,239, herein incorporated by reference. In this system, circulation in a target region of the body may be isolated from the systemic circulation so that the target region circulation is compartmentalized from the systemic circulation while still performing its function for the body. Therapy may therefore be delivered in a manner to maintain a high target region to systemic gradient for an extended period of time. The system employs an inflow channel to fluidically perfuse the target region, and an outflow channel to permit drainage from the target region.

As described above, a valuable application for localized perfusion therapy is the treatment of ischemic myocardium. To retrogradely deliver therapy to the target myocardium via the coronary sinus, the therapy delivery system must consider the net effects of the inflow and outflow, as well as synchronization of the timing of inflow and outflow with respect to physiological cardiac activity. The inflow perfusion is primarily responsible for the therapy delivery, such as myocardial salvage. However, the inflow perfusion can have unintended effects to the venous system and myocardial bed, including increased coronary pressure and myocardial congestion. Increased coronary vessel pressure may induce hemodynamic instability. Additionally, increased coronary vessel pressure can lead to myocardial congestion, which may compromise myocardial perfusion, possibly causing ischemia, which can reduce contractility or lower systemic blood pressure. Myocardial congestion may also increase the risk of ventricular arrhythmias, particularly fibrillation or cardiac arrest.

Additional considerations must be taken when perfusion inflow is cooled to provide myocardial cooling treatment. Bradycardia, a significant heart rate drop, can be the result and the indicator of heart cooling. Lower myocardial temperature may also increase the risk of ventricular fibrillation. Without stringent controls on systemic outflow from the heart, undesired systemic cooling may also result from cooled perfusion inflow.

The potential side effects of perfusion inflow may be mitigated with the fluidic outflow by controlling coronary venous pressure to within a safe range, and in some cases within a normal physiological range. Perfusion systems have heretofore been limited in their ability to monitor and manage respective inflows to and outflows from a target region. Conventional systems often utilize fixed flow rates. As conditions change during treatment, such as a changing heart rate, inflow and outflow volumes may not remain stable, which can dramatically compromise the effectiveness of therapy delivery. An alternative approach is to control the inflow and outflow pulse volumes in an effort to achieve an inflow that exceeds dead space volume in the perfused region, such as the venous volume between the inflow port and the target tissue for treatment. However, frequent arrhythmia and errors in reading heart rate indicators, this approach can cause drastic changes for pump operations.

A need therefore exists for a perfusion flow system that is capable of dynamically controlling inflow and outflow, and particularly relatively controlling inflow and outflow to accommodate changing physiological conditions during treatment, or to accommodate errors in initially estimating perfusion region characteristics like dead space, and flow resistance.

SUMMARY OF THE INVENTION

By means of the present invention, fluidic inflow to and fluidic outflow from a target region in the body may be relatively controlled to dynamically accommodate changing physiological conditions of the body. Various parameters of each of the fluidic inflow and the fluidic outflow, whether continuous or discontinuous, may be controlled, including, for example, flow pulse onset timing, both relative to other flow pulses and/or to any one or more of physiological conditions (such as the heartbeat), flow pulse duration, volumetric flow rate, therapeutic agent concentration, flow temperature, and the like. The dynamic adjustment of flows, both absolute and relative, may be driven by one or more algorithms that are responsive to pre-defined inputs and/or sensed conditions. The sensed conditions may include physiological conditions and physiological event markers.

In one embodiment, a method for controlling fluid flow involves fluid flow in a human heart. The method includes establishing a model cutoff frequency of a system including a coronary target region, wherein the target region is considered a low-pass filter and the model cutoff frequency may include an interval defined by a waveform cycle. The model cutoff frequency may be established in a one-time measurement, periodically, or continuously. An inflow pulse of fluidic inflow is controllably delivered to the target region through the coronary venous system of the heart in an inflow volume within an inflow time period. The fluidic inflow preferably has a therapeutic effect upon the target region. An outflow pulse of fluidic outflow from the target region is controlled in an outflow volume within an outflow time period. A net volume is defined by a difference of the inflow volume and the outflow volume. The fluidic inflow pulse, the fluidic outflow pulse, and any delays therebetween are adjustably controlled. In one embodiment, the flows may be relatively controlled to an adjustable ratio of inflow time period to outflow time period. One or both of the inflow time period and the outflow time period may include a delay time with no flow. A total time period from onset of the fluidic inflow pulse to termination of the fluidic outflow pulse may be controlled to be greater than the cycle interval at the cutoff frequency of the target region.

In some embodiments, the onset of the fluidic inflow pulse and an onset of the fluidic outflow pulse are relatively controlled, and may be relatively controlled based upon a physiological time period. The physiological time period may be a heartbeat, wherein the heartbeat may be defined from a first systole onset to an immediately subsequent systole onset.

In some embodiments, the system is operated such that the heartbeat rate is less than the model cutoff frequency. A flow cycle may be defined by the onset of the fluidic inflow pulse to the termination of the fluidic outflow pulse, including any "delay" periods with no flow, and a flow cycle duration is measured with respect to the heartbeat. A flow cycle frequency is determined as the heartbeat divided by the number of heartbeats in the flow cycle, and the flow cycle frequency is preferably less than the model cutoff frequency.

In some embodiments, the inflow time period includes one or more consecutive diastole periods, and the outflow time period includes one or more consecutive systole periods. The fluidic inflow pulse and the fluidic outflow pulse may be controlled at fixed flow rates or fixed flow volumes. The model cutoff frequency of the target region may be approximated to be proportional to an inverse of a product of a fluidic flow resistance of the target region and a compliance of the target region, and particularly a fluidic flow resistance and compliance of the target myocardium and associated vascular volume.

The model cutoff frequency may be established by measuring a frequency response of the subject structure that exhibits flow resistance and capacitance. In preferred embodiments, the fluidic inflow is greater than a dead space volume of the subject structure.

The adjustable ratio of fluidic inflow to fluidic outflow may be controlled in two or more priority conditions. A first priority condition prioritizes the therapeutic effect, and a second priority condition prioritizes maintaining at least one of a pressure and a temperature of the target region within a respective predetermined pressure range and temperature range. Switching between the first and second priority conditions, potentially among many priority conditions, may be dependent upon feedback of therapy delivery and/or adverse effects of therapy delivery, such as from temperature and pressure measurements in the target region.

A therapy delivery system may be configured to deliver a therapeutic agent to a target region in a body. The delivery system may include an inflow channel for conveying the therapeutic agent to the target region, and an outflow channel for conveying the fluid from the target region. A monitor apparatus may be used with the delivery system to monitor a control condition with a sensor, and to generate a respective system feedback signal indicative of the control condition. The control condition may include a physiological condition of the body that is affected by at least one of the therapeutic agent and a volumetric flow rate of fluid through the outflow channel. The therapy delivery system further includes a controller for controlling flow through the inflow channel and the outflow channel, and is responsive to the system feedback signal to adjust flow through one or more of the inflow channel and the outflow channel to an extent suitable to treat or prevent adverse cell changes to the target region. Adverse cell changes may include cell apoptosis and cell death.

The sensor of the monitor apparatus may be adapted to sense fluid pressure in the target region, and to emit the system feedback signal that is indicative of the fluid pressure. The flows through the respective inflow and outflow channels may be adjustable to regulate fluid pressure in the target region in accordance with a pre-determined pressure profile. In some embodiments, the pressure profile includes a maximum pressure threshold. The sensor may in particular be adapted to sense coronary vessel pressure.

The controller may be configured to operate a flow regulator to adjust flow through one or more of the inflow channel and the outflow channel. The flow regulator may be selected from one or more of a pump, a valve, and an expandable occlusion device.

The control condition may be selected from one or more of target region fluid pressure, target region temperature, inflow volumetric flow rate, outflow volumetric flow rate, time, inflow fluid temperature, outflow fluid temperature, body temperature, a physiological event marker, coronary vessel pressure, heartbeat rate, and electrocardiogram changes. The physiological event marker may be systole onset. The controller may be adapted to drive the flow regulator in a manner to create a pulse of fluidic inflow having an inflow pulse onset that is coordinated with the diastole onset. In some embodiments, the inflow pulse onset may be subsequent to the diastole onset. In some embodiments, the pulse duration of the fluidic inflow may be longer than an event interval of the heartbeat, which may be a cycle time between the systole onset of a first heartbeat and the systole onset of an immediately subsequent heartbeat. The pulse duration and a pulse interval may preferably be adjustable by the controller.

Another therapy delivery system may include an inflow channel for conveying fluidic inflow including a therapeutic agent to a target region, and an outflow channel for conveying fluidic outflow from the target region. A first flow regulator is arranged to adjust flow through the inflow channel, and a second flow regulator is arranged to adjust flow through the outflow channel. The therapy delivery system includes a controller for controlling the first and second flow regulators to effect a therapeutic effect of the therapeutic agent to the target region. The controller is preferably adapted to drive the first and second flow regulators in coordination with a control algorithm for each of an inflow pulse and an outflow pulse. The control algorithm assigns an operating parameter including at least one of a pulse onset, a pulse duration, and a pulse end for each of the first and second flow regulators. The operating parameter is preferably assigned according to a time schedule of the control algorithm that corresponds to a heartbeat, and a ratio of the fluidic inflow to fluidic outflow is adjustable.

A method for delivering a therapeutic agent to a target region in a body includes monitoring a control condition related to a physiological condition of the body, and delivering a fluidic inflow including the therapeutic agent to the target region. The method further includes conveying a fluidic outflow from the target region responsive to the control condition, wherein fluidic inflow, fluidic outflow, and timing and time duration thereof are relatively adjustable to accomplish a desired net flow and absolute flow. A characteristic parameter of the fluidic inflow may be dynamically adjusted, wherein the characteristic parameter may include one or more of therapeutic agent concentration in the fluidic inflow, and fluidic inflow temperature. The control condition may be selected from one or more of target region fluid pressure, target region temperature, inflow volumetric flow rate, outflow volumetric flow rate, inflow fluid temperature, outflow fluid temperature, a physiological event marker; coronary vessel pressure, heartbeat rate, time, and electrocardiogram changes.

DETAILED DESCRIPTION OF THE PREFERRED EMBODIMENTS

Figure 1:
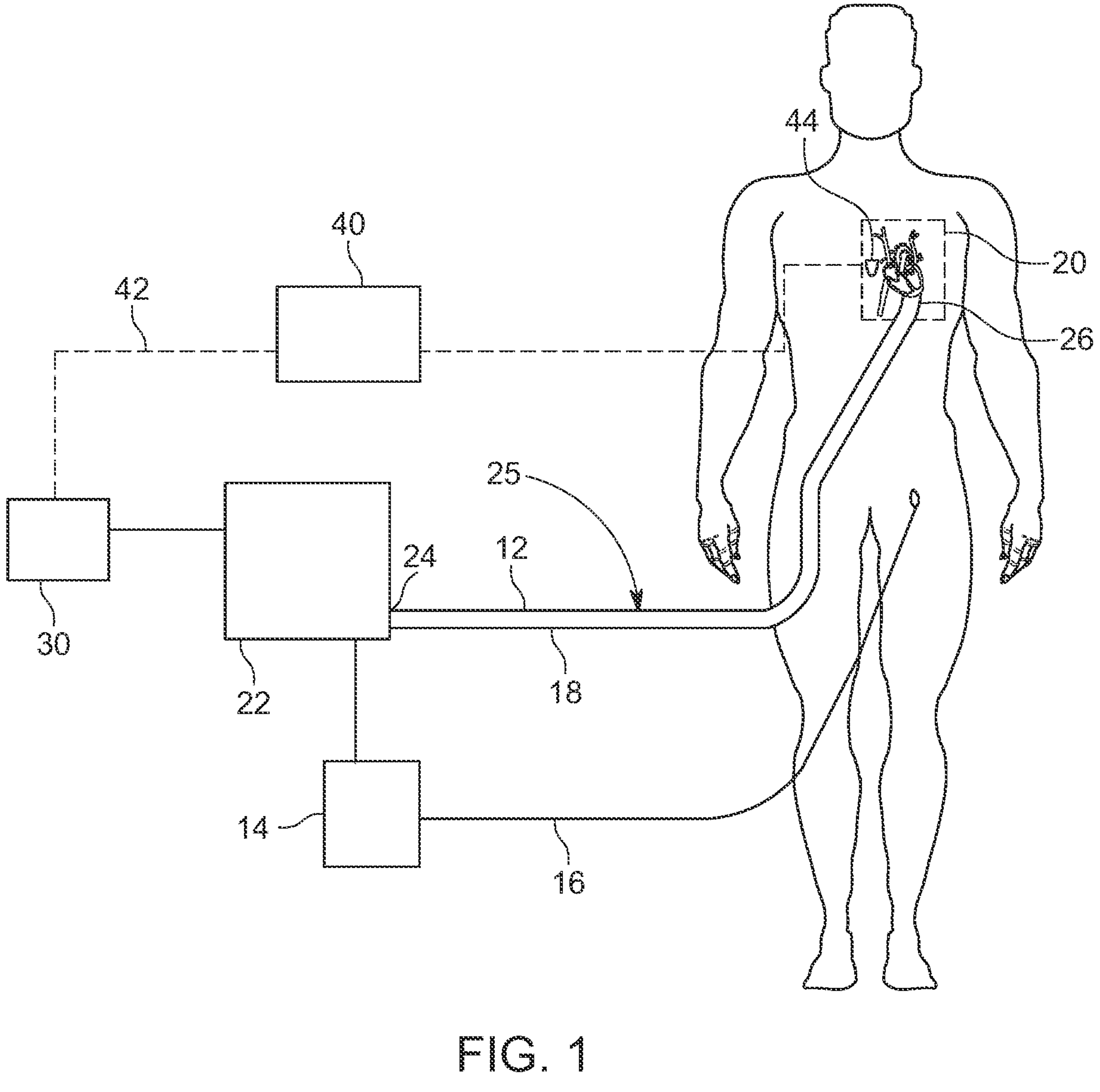
FIG. 1 is a schematic illustration of a therapy delivery system of the present invention.

The objects and advantages enumerated above, together with other objects, features, and advances represented by the present invention will now be presented in terms of detailed embodiments described with reference to the attached drawing figures which are intended to be representative of various possible embodiments of the invention. Other embodiments and aspects of the invention are recognized as being within the grasp of those having ordinary skill in the art.

An aspect of the present invention is the delivery of therapy to a target region in the human body. In some embodiments, the target region may be at least partially isolated from the systemic circulation of the body. For the purposes of the present invention, the term "target region" may mean a region of cells and/or a cell structure of a human body, such as an organ or limb having blood circulation therethrough. A particular example of a target region may be a human heart, which, for the purposes of this disclosure, is intended to include the tissues and structures that are generally considered to comprise a component of or an integral to the heart organ, including, for example, the myocardium, epicardium, endocardium, coronary sinus, atria, ventricles, valves, aorta, pulmonary artery, and coronary arteries and veins. For the purposes hereof, the term "systemic" is intended to mean the overall blood circulation of the human body.

The delivery of therapy to a target region may be conducted through blood conduits in the body. The therapy delivery of the present invention may be conducted through one or both of the venous and arterial systems of the body. Various applications of therapeutic delivery are envisioned for the present invention, such as therapeutic hypothermia, oxygenation, drug delivery, and cell-based therapy. The delivered therapy may also be in the form of deactivation, such as warming cooled blood and tissues to physiological temperatures, metabolizing bioactive agents to minimize or eliminate toxins in the bioactive agents, and adding compensatory agents to neutralize systemic activity of bioactive agents employed in the therapy.

In some embodiments of the present invention, blood circulation in a target region of the body may be partially or substantially completely isolated from the systemic circulation. Apparatus for fluidic delivery to and drainage from a target region in the body is described in, for example, U.S. Pat. No. 11,173,239, assigned to the present assignee and herein incorporated by reference in its entirety. The apparatus of U.S. Pat. No. 11,173,239 provides an extracorporeal blood loop to condition autologous blood for perfusion through the target region. The blood conditioning apparatus may include a flow-volume adjusting mechanism to regulate or equate input and output fluid volumes to the target region. The flow-volume adjusting mechanism monitors input/output balance, and is adapted to selectively add or remove fluid from the perfusion loop. Balancing blood may be sourced from the systemic circulation of the body.

Flow direction of inflow to the target region may be antegrade (artery to vein) or retrograde (vein to artery). In some embodiments, retrograde perfusion of the target region may be preferred for access to post-occlusion ischemic tissue. Retrograde perfusion flow may additionally minimize arterial damage and the potential for debris occlusion through arterial embolism. As will be described herein, perfusion flow rate and timing may be controlled to optimize therapy delivery while minimizing potential adverse effects of perfusion flow to the target region.

A schematic illustration of a therapy delivery system of the present invention is provided in FIG. 1. The system 10 is preferably adapted to deliver a therapeutic agent from a source 14 to a target region 20 in a human body. The therapeutic agent may include one or more of a variety of substances and/or treatments that effect therapy or deactivation to target region 20. Example therapeutic agents include, for example, oxygen, a bioactive drug or material, and a temperature. Source 14 of the therapeutic agent may therefore comprise a reservoir for a bioactive drug or material, an oxygenator for oxygenating a fluid, or a heat exchanger for heating and/or cooling a fluid. In some embodiments, source 14 may supply autologous blood to system 10 from the body through a source line 16 that is fluidically connected to, for example, a venous vessel in the body. Source line 16 may include a catheter or other structure capable of conveying blood from the body to source 14.

System 10 includes an inflow channel 12 for conveying the therapeutic agent to target region 20 ("inflow"), and an outflow channel 18 for conveying fluid from target region 20 ("outflow"). Inflow channel 12 and outflow channel 18 may respectively comprise lumens in one or more catheters or other structure that form a conveyance pathway for fluid to be guided between target region 20 and a fluid handling apparatus 22. In some embodiments, inflow channel 12 and outflow channel 18 may be contained in a single transvenous catheter positioned with a proximal end 24 fluidically coupled to fluid handling apparatus 22 and a distal end 26 in or adjacent to target region 20. Distal end 26 may, in some embodiments, be operably positionable in a venous drainage structure of target region 20. For example, distal end 26 of catheter 25 may be operably positionable in a coronary vessel of a heart, wherein the heart and associated vasculature comprises the target region 20.

In some embodiments, inflow channel 12 and outflow channel 18 may be separately introduced into the body in distinct introduction structure, such as in distinct catheters. The catheters may be positioned in venous or arterial pathways. For example, system 10 may employ a first catheter for inflow channel 12 and a second catheter for outflow channel 18. One or both of the catheters may be introduced into the body venously or arterially. In other embodiments, inflow channel 12 and outflow channel 18 may share a lumen with bi-directional flow.

Each of inflow channel 12 and outflow channel 18 may include one or more ports for delivery and/or intake of fluid. In some embodiments, inflow channel 12 and outflow channel 18 each include one or more ports at distal end 26 of catheter 25 for delivering inflow to target region 20, and for receiving outflow from target region 20. Either or both of inflow channel 12 and outflow channel 18 may utilize part or all of an inflow access or an outflow access of target region 20. The inflow and outflow accesses of target region 20 may be separate or shared.

Fluid handling apparatus 22 may include pumps, valves, channels, reservoirs, heat exchangers, oxygenators, bioactive agent reservoirs and pumps, flow diverters, flow junctions, bubble traps, and the like to manipulate inflow and outflow. Components that are capable of adjusting or impacting a volumetric flow rate through inflow channel 12 or outflow channel 18, such as pumps, valves, occlusion devices, diverters, and junctions may be considered flow regulators. Components that are capable of changing a chemical or physical property of the fluidic inflow or the fluidic outflow itself, such as oxygenators, heat exchangers, and bioactive agent suppliers may be considered flow enhancers. Fluid handling apparatus 22 therefore may include one or more flow regulators and flow enhancers.

Operation of fluid handling apparatus 22 may be controlled by a controller 30. In some embodiments, controller 30 may include an input device such as a keyboard, remote pointer device, touch screen, or other suitable input means, a graphical user interface, a processor drivable by software and/or firmware communicatively linked to the processor, a database communicatively linked to the processor, a signal receiver for receiving signals from one or more sensors, relays, amplifiers and the like, and a signal generator for generating and transmitting control signals to fluid handling apparatus 22. Preferably, control software including logic algorithms may be stored in or accessible to the controller database and/or processor. Controller 30 is preferably adapted to control fluid handling apparatus 22 in achieving desired characteristics for the inflow and the outflow.

System 10 may further include a monitor apparatus 40 for monitoring a control condition and generating a feedback signal 42 indicative of the control condition. The feedback signal 42 may be communicated to controller 30 to adjust settings of fluid handling apparatus 22 to maintain or achieve control condition set points. The control condition may include a physiological condition of the body. In some embodiments, the physiological condition monitored by monitor apparatus 40 may be affected by at least one of the therapeutic agent and a volumetric flow rate of fluid through one or both of inflow channel 12 and outflow channel 18. Example control conditions that include such a physiological condition include a target region fluid pressure, a target region temperature, inflow volumetric flow rate, outflow volumetric flow rate, inflow fluid temperature, outflow fluid temperature, a physiological event marker, coronary vessel pressure, heartbeat rate, and electrocardiogram output.

Monitor apparatus 40 may include a sensor 44 for sensing the control condition and transmitting a signal indicative of the sensed control condition. Example sensors 44 useful for monitor apparatus 40 include thermocouples, pressure transducers, orifice plates, flow meters, such as ultrasonic flow meters, magnetic flow meters, vortex flowmeters, and positive displacement flow meters, heartrate monitors, and electrocardiograms. It is to be understood that various sensing means may be employed in connection with monitor apparatus 40 to dynamically or statically determine one or more control conditions.

An example control condition useful in the present invention is fluid pressure in target region 20. In this embodiment, sensor 44 may be a pressure transducer to sense fluid pressure in target region 20. In the case of the heart being target region 20, sensor 44 may be arranged to sense coronary vessel pressure. Controller 30 may be adapted adjust inflow and outflow via fluid handling apparatus 22 to regulate fluid pressure in target region 20 in accordance with a pre-determined pressure profile and the sensed pressure. For example, reducing pressure in target region 20 may be accomplished by one or more of reducing volumetric inflow rate, increasing volumetric outflow rate, reducing inflow pulse duration, increasing outflow pulse duration, adjusting the relative timing of the inflow and outflow pulses, and combinations of one or more of such parameters. An example pressure profile is a maximum pressure threshold, wherein controller 30 controls fluid handling apparatus 22 to maintain the sensed pressure at target region 20 below the maximum pressure threshold. Pressure profiles other than a maximum pressure threshold, however, are contemplated as being useful in the present invention. An example pressure profile is a pressure range between a minimum pressure threshold and a maximum pressure threshold. Pressure profiles may also include gradients that prioritize certain pressure ranges over other pressure ranges. Moreover, pressure profiles may include temperature dependencies that adjust target pressure ranges based on sensed temperatures. Pressure profiles may be dynamically adjustable to accommodate changing physiological conditions. For example, a permissible maximum pressure threshold may be different during systole than during diastole. Pressure profiles may also relate to timed-average pressure measurements in addition to or in place of instantaneous pressure measurements.

In some embodiments, controller 30 may be responsive to a control condition that is not itself a physiological condition, such as time. System 10 may include a timer that is capable of transmitting a timing signal to controller 30, wherein a control algorithm using time as a determinative variable may be executed by controller 30 with the timing signal received from the timer. The timing signal may be related to an expected or sensed physiological condition. For example, the timing signal may be related to a heartbeat, such as an onset of systole. The timing signal may be generated based upon an expected timing of systole onset, and intervals of the timing signal may be fixed or adjustable, with adjustable timing signal intervals being based upon one or more sensed physiological conditions. The sensed physiological signals that may be used by controller 30 to adjust timing signal intervals may include, for example, those physiological conditions described above which themselves may comprise control conditions.

Physiological conditions and/or event markers may be sensed by appropriate sensors 44, and the resultant feedback signals 42 may be directly used by controller 30 as a control condition, or may be indirectly used to adjust a control condition, such as a timing signal. The term "events" may mean the periodical or cyclical physiological change of the target region or the body. An example event is a heartbeat or a cardiac cycle. An "event marker" is a signal or a combination of signals from the target region or the body that indicates a point in time for each period or cycle of the event. In some cases, the event marker indicates an event onset. An example event marker is a heart systole onset, which may be determined by sound wave, electrocardiogram signal (r-wave), left ventricular pressure, pulse oximetry, and the like. The duration of each event cycle is referred to as an event interval. In the case of the heart, an example event interval may be the heartbeat, defined as the time period from systole onset to diastole termination, including any delay between systole termination and diastole onset. Other example event intervals include systole and diastole individually.

Controller 30 may preferably control fluid handling apparatus 22 to permit or drive inflow an outflow through respective inflow channel 12 and outflow channel 18 in accordance with one or more fluid flow algorithms. In some embodiments, the fluid flow may be conveyed over a specific time period in a "pulse". A pulse duration is defined as a time period from the pulse start to the pulse end. The fluidic volume produced in each pulse defines a "pulse volume". For the purposes hereof, a "pulse profile" may mean a specific flow velocity profile for each stroke, and an "average flow" may mean the average flow rate of the flow, taking into account the pulse profile and pulse duration.

In some embodiments, pulse onsets for the inflow and the outflow may be synchronized to the same or to different event markers. A synchronization phase may be defined as the time lag or delay of the pulse onset from the event marker. A positive synchronization phase means that the pulse onset occurs after the event marker, while a negative synchronization phase means that the pulse onset occurs before the event marker.

Controller 30 may be programmed to predict a timing of an event onset and of an event interval, based upon data acquired from one or more previous cycle durations. As a result, subsequent pulse onsets may be set to occur in relation to a predicted event onset. In some embodiments, a subsequent pulse onset may be set to occur prior to a corresponding event onset, to operate in a negative synchronization phase. Moreover, the pulse profile and pulse duration may be determined by controller 30 to maintain a programmed average flow, pulse volume, or both. The inflow pulse and outflow pulse may be delivered simultaneously or sequentially, with the pulse onsets and durations synchronized with the same or different event markers, or the same or different events. In one embodiment, inflow onset may be synchronized with an event onset, while outflow onset may be timed in relation to the inflow onset.

Applicants contemplate both synchronous and non-synchronous modes of operation for controller 30 of system 10. A synchronous mode for controller 30 is responsive to an event or an event marker, while a non-synchronous mode for controller is responsive to a physiological condition, a fixed timing sequence, and/or an adjustable timing sequence. Each mode type may be operated under different levels of user input control and pre-determined parameters that may be adjusted with acquired data.

A common application of the present invention is the therapeutic treatment of a coronary target region, such as through perfusion of oxygenated and/or temperature-controlled blood. In this application, the therapeutic agent may be the oxygen added to the blood and/or the reduction of thermal energy in the blood (cooled). Therapy delivery to the heart as the target region is often accomplished with one-way access through the venous coronary vasculature that is commonly shared by the inflow and outflow. The common volume in the coronary vessel and perfused myocardium represents a dead space that can significantly decrease the efficiency and effectiveness of the therapy delivery. This is of particular concern where the inflow and outflow pulse volumes are significantly smaller than the dead space volume.

Figure 2:
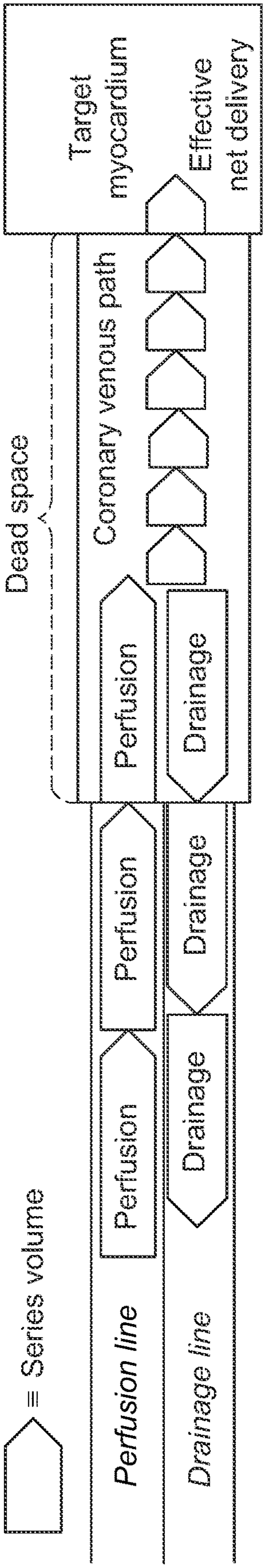
FIG. 2 is a schematic illustration of dead space in a coronary venous pathway for inflow and outflow in a fluidic therapy delivery system.
Figure 3:
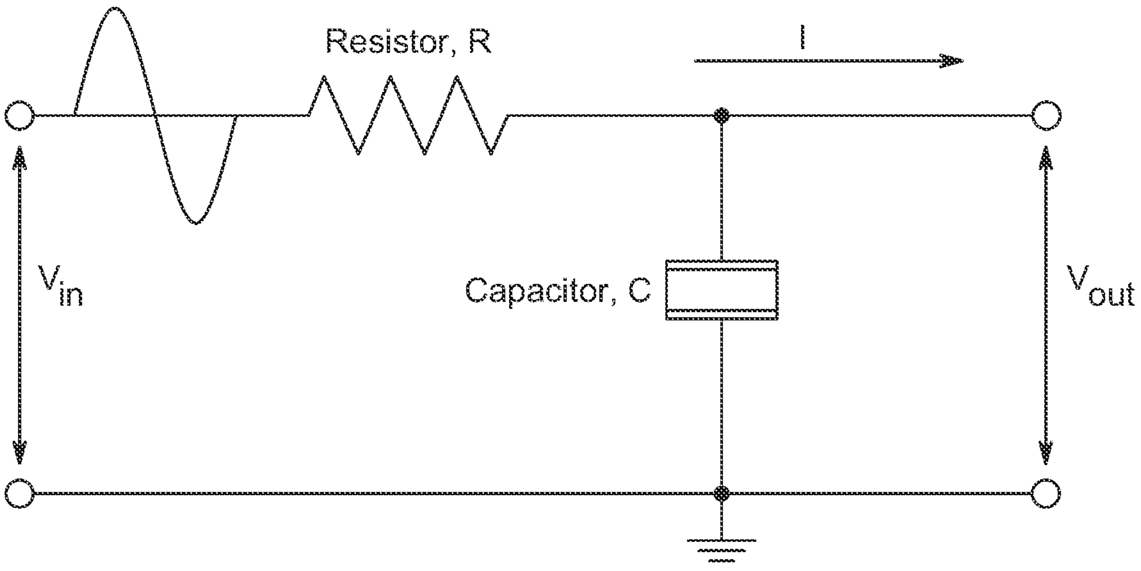
FIG. 3 illustrates a basic low-pass filter design.

FIG. 2 is a schematic representation of dead space in a coronary venous pathway for perfusion and drainage in a fluidic therapy delivery system. The dead space, including the coronary veins, also adds significant flow compliance to the delivery pathway due to their high degree of elasticity. Given the compliance introduced by elastic structures in the target region, as well as the inherent flow resistance through such structures, an aspect of the present invention is to program controller 30 as though the target region represents a low-pass filter. A low-pass filter is a circuit that can modify, re-shape or reject all unwanted high frequencies, and accept or pass only those signals below a frequency threshold. The frequency threshold is commonly referred to as the "cutoff frequency". FIG. 3 illustrates a basic low-pass filter for electrical applications.

Applicants have designed controller 30, in one embodiment, to treat target region 20 as a low-pass filter. The "frequency" of therapy delivery system is a cycle of an inflow pulse and an outflow pulse, with the volume of each pulse representing the amplitude of a waveform cycle. The natural frequency of the system including target region 20 therefore becomes a controlling factor in how to effectively deliver therapy to target region 20. Other factors include compliance of the system created by the volumes of the flow loop and the catheter. Above a threshold (cutoff) frequency of fluidic inflow/outflow pulses, amplitude of perfusion to target region 20 diminishes dramatically. Cutoff frequency of a low-pass filter is determined by the following relationship:

$$f_c = 1/2\pi RC$$

wherein: R=resistance
C=capacitance

Figure 4:
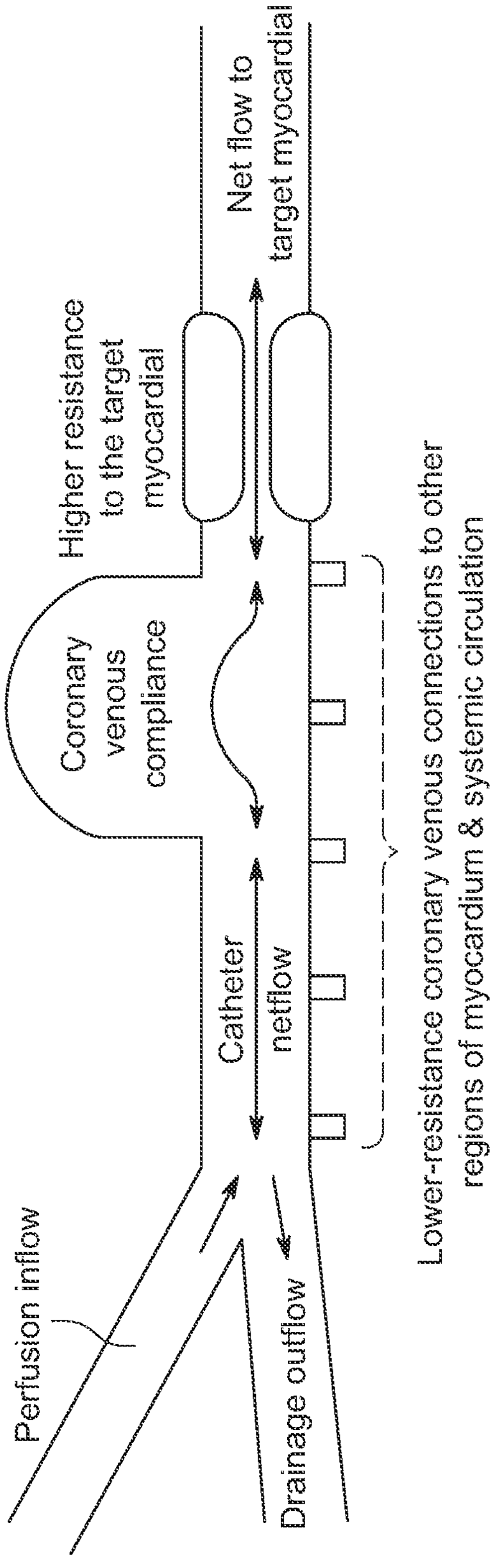
FIG. 4 is a schematic illustration of system net flow relative to myocardial net flow as a function of venous compliance and myocardial resistance.

To maintain the flow cycle frequency in a desired range with respect to the cutoff frequency, the total time period from onset of the inflow pulse to the termination of the outflow pulse, including any delay from the end of the inflow pulse to the beginning of the outflow pulse, and any delay from the termination of the outflow pulse to the onset of the next inflow pulse, should be greater than a cycle interval (complete waveform cycle) of the cutoff frequency. In the case of target region 20 comprising a heart, the cutoff frequency may typically be much greater than the heartrate. Another relationship useful in programming controller 30 for applications in which target region 20 comprises the heart is as follows:

$$\text{Flow Cycle Frequency} = \text{Heart Rate/Total Heartbeats per Flow Cycle} \ll \text{Cutoff Frequency}$$

wherein: Heart Rate=beats/min
Flow Cycle Frequency=cycles/min
For example:
Heart Rate=60 beats/min
Flow Cycle=inflow pulse for 2 heart beats; off for 0 beats; outflow pulse for 1 heart beat
=(2+0+1+0)−1=2 cycles
(wherein subtractor of −1 is derived from the first inflow pulse or outflow pulse is ½ of heart beat)
Flow Cycle Frequency=60/2=30 beats/min Controller 30 is therefore programmed to adjust the inflow pulse and the outflow pulse relative to one another in order to meet the flow cycle frequency limitation of being less than the cutoff frequency of target region 20. Given the definition of cutoff frequency, increased coronary compliance decreases cutoff frequency. FIG. 4 schematically illustrates system net flow relative to myocardial net flow as a function of venous compliance and myocardial resistance.

Applicants have observed a significant difference in net flow to target region 20 between non-ischemic tissue and prolonged ischemic tissue. In the case of non-ischemic, healthy tissue, net therapeutic flow is rapid and effective, even with relatively large dead space and compliance in the coronary venous system. Therapeutic flow through ischemic tissue, by contrast, was significantly restricted. Prolonged ischemia can cause tissue inflammation, which results in a significant increase in myocardial blood channel flow resistance. The increased flow resistance also decreases cutoff frequency, resulting in attenuation of the therapeutic inflow to the heart.

A common response to limited therapeutic net inflow to target region 20 may be to increase the inflow volumetric flow rate. However, it has been discovered that doing so can lead to increased target region pressure. In the case of the heart as the target region, increased coronary vessel pressure can lead to myocardial congestion. These effects may reduce the cutoff frequency of the target region, which can compromise the effectiveness of myocardial perfusion. As a result, controller 30 is preferably adapted to dynamically adjust perfusion inflow and drainage outflow, both individually and relatively, as well as to adjust delay between respective inflow and outflow portions of the cycle, to maximize the therapeutic effect of the perfusion. Such adjustment may involve minimizing congestion of the target region by increasing drainage outflow. Controller 30 therefore may continually optimize an inflow to outflow cycle ratio in response to predicted and/or sensed conditions, such as the control conditions described above.

Figure 5:
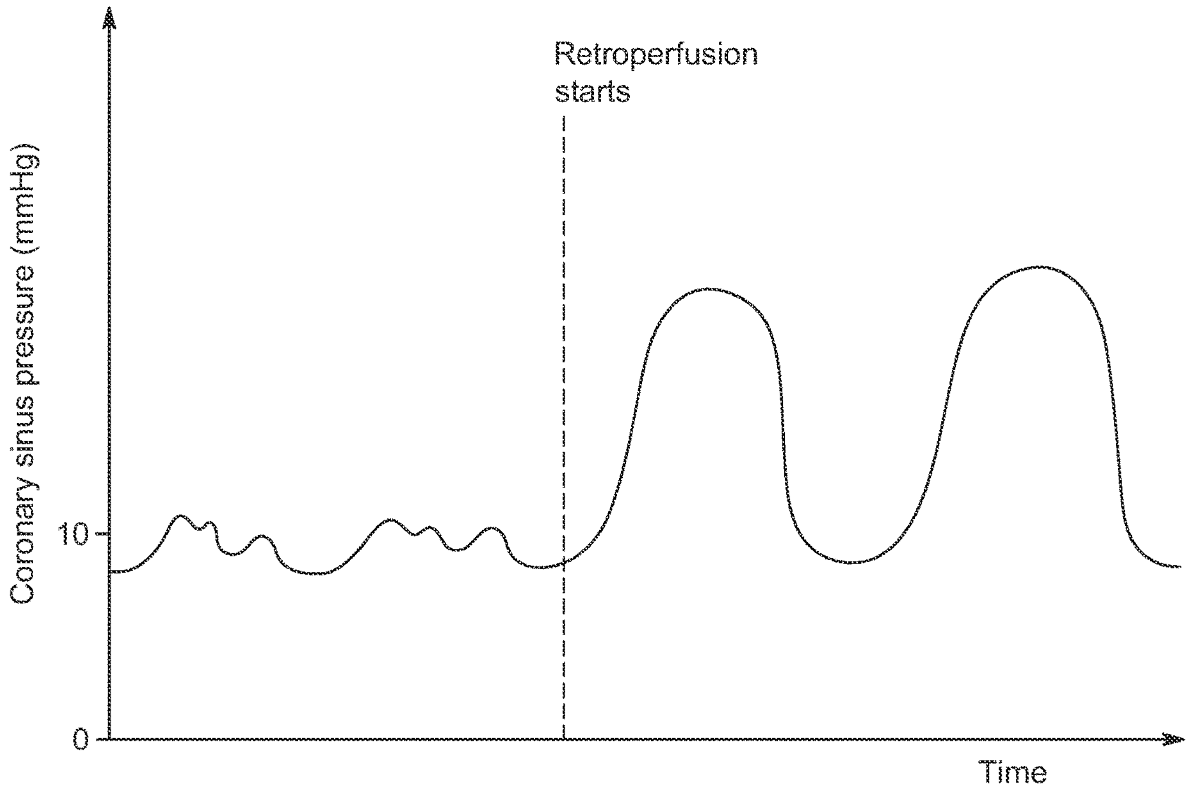
FIG. 5 is a graphical depiction of coronary venous pressure fluctuation before and during therapeutic retroperfusion.

Physiological coronary venous vessel pressure fluctuates throughout each cardiac cycle, but typically within a narrow range of 5-15 mm Hg. Pressures in arterial vessels would be different. Increased coronary vessel pressure is anticipated with the inflow perfusion therapy of the present invention. FIG. 5 is an illustration of how coronary venous pressure fluctuates before and during therapeutic retroperfusion, with pressure peaks representing inflow periods, and pressure troughs representing outflow periods. In some embodiments, maximum coronary venous pressure may be maintained below 100 mm Hg, and preferably below 50 mm Hg. Moreover, minimum coronary venous pressure may be maintained below a threshold at which adverse physiological effects may arise. In some embodiments, minimum coronary venous pressure may be maintained between a normal physiological pressure and a safety threshold retroperfusion pressure.

To ensure that the flow cycle frequency remains less than the cutoff frequency, the inflow pulse and the outflow pulse may be relatively controlled to an adjustable ratio of inflow time period to outflow time period, wherein a total time period from onset of the inflow pulse to termination of the outflow pulse, plus any delay time period between the pulses, may be greater than an interval of the cutoff frequency of the coronary target region, which includes the associated coronary veins. For example, the total time period from inflow pulse onset to outflow pulse termination, including any delay between inflow pulse termination and outflow pulse onset, as well as any delay between the outflow pulse and the next inflow pulse, may be longer than a heartbeat. The heartbeat may be defined from a first systole onset to an immediately subsequent systole onset.

Controller 30 may preferably be programmed to adjust, both individually and relatively, inflow pulse and outflow pulse onsets, durations, and volumetric flow rates. In some embodiments, the onset of the inflow pulse and the onset of the outflow pulse may be relatively controlled based on a physiological time period, such as a heartbeat of the heart. Controller 30 may therefore operate upon an adaptive algorithm that adjusts control of fluid handling apparatus 22 dynamically in response to changing conditions, such as changing heart rates, model cutoff frequencies, target region pressures, target region temperatures, and the like. In some embodiments, a flow cycle of system 10 may be defined by the onset of the fluidic inflow pulse to the termination of the fluidic outflow pulse. A flow cycle duration, in the case of target region 20 comprising the heart, may be measured with respect to the heartbeat. A flow cycle frequency may therefore be determined as the heartrate divided by the number of heartbeats in the flow cycle. Controller 30 may preferably assign the flow cycle frequency as being less than the cutoff frequency.

In other embodiments, the onsets and intervals of the inflow and outflow may be predefined and/or not based upon a physiological time period. A flow cycle in these embodiments may be defined by the onset of the fluidic inflow pulse to the termination of the fluidic outflow pulse. The flow cycle is preferably less than the cutoff frequency.

It is contemplated that the cutoff frequency for the system, including the target region 20, such as the heart may be modeled through one or more of a number of techniques. In the case of the heart, the cutoff frequency is the fluid dynamic and mechanical properties of the venous compartment into which the perfusion is directed. The two key factors in determining cutoff frequency are: (1) the combined vascular compliance from the occlusion device sealing the perfusion compartment to the myocardium; and (2) the myocardial resistance. Altering the position of the catheter, either intentionally or via migration therefore will also affect the cutoff frequency. A first technique to model the cutoff frequency may involve an iterative process in which an outcome of the therapy delivery is monitored for compliance with or deviation from an expected outcome. An example expected outcome of the therapy delivery may be a coronary vessel pressure or pressure range. Initial measurements of coronary vessel pressure below the minimum threshold pressure or pressure range may, for example, cause controller 30 to increase inflow pulse duration or inflow volumetric flow rate relative to outflow pulse duration or outflow volumetric flow rate. Conversely, initial measurements of coronary vessel pressure above the maximum threshold pressure or pressure range may, for example, cause controller to decrease inflow pulse duration or inflow volumetric flow rate relative to outflow pulse duration or outflow volumetric flow rate. Controller 30 may consider pressure measurements, derived from signals from sensor 44, at various intervals to continue to relatively adjust inflow and outflow until the measured pressure is within a pre-defined range. The flow cycle frequency reached when the measured condition is within the pre-defined range becomes an estimation of a model cutoff frequency.

As heart rate changes, the ratio of inflow to outflow may also require adjustment in order to maintain the real-time flow cycle frequency below the model cutoff frequency. In addition, since the catheter position and myocardial resistance may change over time during therapy delivery, establishment of the model cutoff frequency may be re-estimated periodically according to the procedure described above. In some embodiments, the flow cycle frequency may be adjusted only upon condition changes of a significant magnitude. For example, the flow cycle frequency may be adjusted only when the heartrate changes, either positively or negatively, by more than one-half of the reference cutoff frequency. It is contemplated that various parameters for frequency of inflow/outflow ratio adjustment may be employed by the present invention.

Example Cutoff Frequency Adjustment by Iterative Process

Initial heart rate=90 beats/min

Model cutoff frequency=inflow pulse for 2 heartbeats; off for 1 heartbeat;

outflow pulse for 1 heartbeat; (2+1+1)−1=90/3=30 beats/min

Changed heart rate=150 beats/min

Adjusted flow cycle frequency<model cutoff frequency;

Adjusted flow cycle = 150 beats/min/30 beats/min = 5 heartbeats

As model cutoff frequency may be periodically assessed, any change in the model cutoff frequency would imply a change in the myocardial resistance, assuming no change in the venous compliance. The implied change in myocardial resistance may itself be instructive to the effectiveness of the therapy delivery, and the need for adjustment thereto.

Another technique for establishing a model cutoff frequency of the system may be through direct measurement of a frequency response to an input signal. Both input and output signals in a time domain may be analyzed and transformed to a frequency domain, such as through a Fourier transformation. The frequency spectrum that the output-input gain attenuates may be noted as the model cutoff frequency. An example of input/output signals for direct measurement of target region frequency response may be pressure measurement at two spaced apart locations in the target region. In some embodiments, a first measurement location may be proximate to an outlet port of inflow channel 12 in target region 20, and a second measurement location may be distal to the outlet port in target region 20. The first and second measurement locations may, for example, be positioned along a perfusion axis, defined as a primary pathway of perfusion flow from the outlet of inflow channel 12 in target region 20. In the case of target region 20 being the heart, pressure values may be measured at two distinct locations in the coronary venous compartment.

A model cutoff frequency range may also be established by measuring directly from previously-obtained experimental data, whether obtained in vivo, ex vivo, or in vitro. The measurements may include, for example, pressure measurements, input flow signals, and output flow signals of the target region, such as the heart.

In some cases, the cutoff frequency may be directly calculated based on determined values for target region compliance and resistance. It is anticipated, however, that obtaining such values may be impractical, and that the true system behavior may be more complex (higher order) than a first-order low-pass filter model.

A variety of parameters may be useful to ascertain the effectiveness of therapy delivery through use of system 10 of the present invention. Chemical sensors may be delivered by and/or connected to a catheter for positioning at target region 20. Such chemical sensors may be adapted to detect chemical species including oxygen, carbon dioxide, inflammatory cytokines, nitric oxide, and the like. Electrocardiogram monitoring may be performed to ascertain changes as therapy progresses, including ST segment elevation and inverted T-wave signals. Coronary venogram and transthoracic Doppler echocardiography are additional tools to determine coronary flow velocities.

Figure 6:
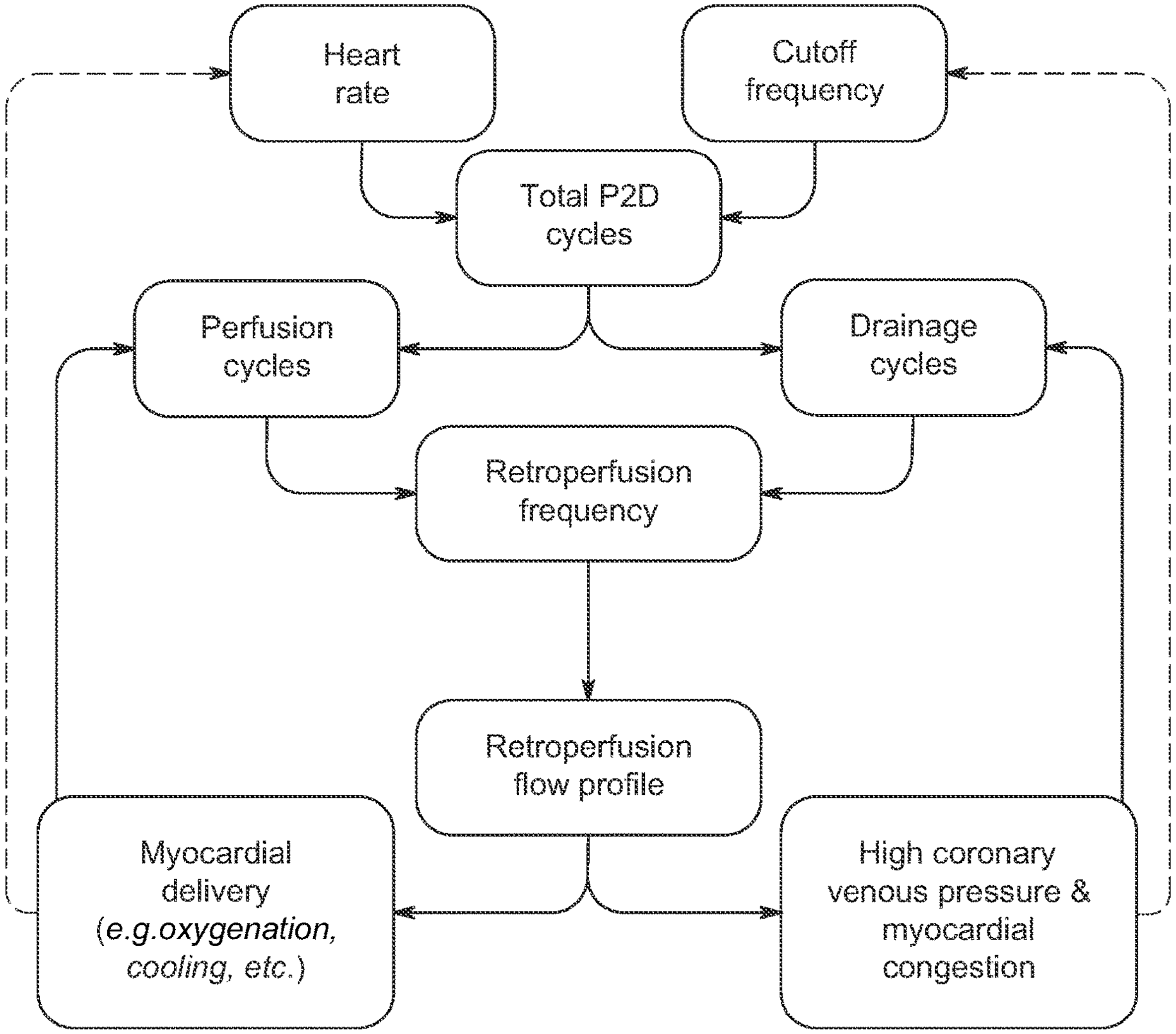
FIG. 6 is a schematic illustration of adaptive control of inflow and outflow to optimize therapy delivery while minimizing adverse physiological effects.

In general, the adaptive control algorithm or algorithms employed by controller 30 may adjust the inflow and outflow in response to changing conditions or passage of time. FIG. 6 schematically illustrates adaptive control of inflow and outflow that is aimed to optimize therapy delivery while minimizing adverse physiological effects. It is understood, however, that such priorities may be contradictory in practice, and unattainable by a single control setting. The present invention therefore contemplates a multi-modal control scheme for controller 30, in which controller may switch among two or more priority operation conditions to more effectively balance the competing priorities of maximized therapy delivery and minimized adverse physiological effects of the therapy delivery. In some embodiments, therefore, controller 30 may control an adjustable ratio of inflow to outflow in two or more priority conditions. A first priority condition may prioritize therapeutic effect of the therapy delivery by focusing upon sufficient inflow to achieve therapy thresholds such as temperature, oxygenation, bioactive drug concentration, and the like. A second priority condition may prioritize maintaining at least one of a pressure and a temperature of target region 20, such as a coronary vessel, within predetermined pressure and temperature ranges. Controller 30 may be programmed to switch among the priority conditions based upon various criteria, such as time and thresholds of the control conditions. Additional priority conditions may include therapy delivery cessation, no switching, and combinations of the priority conditions.

Controller 30 may further be programmed to intermittently cause an outflow pulse to adjust a pressure in target region 20 to a target pressure or pressure range. The intermittent outflow pulse may be separate from the adjustable inflow to outflow ratio algorithm described above, and may instead be treated as an intermittent correction outflow pulse to decompress target region 20. Such decompression may improve tissue washout and may minimize the risk of tissue congestion. The intermittent outflow procedure may further allow for diagnosis of the native coronary venous return, such as coronary-venous blood gas for myocardial oxygen consumption and metabolite.

The control algorithm utilized by controller 30 may assign an operating parameter including at least one of a pulse onset, a pulse duration, and a pulse end for each of the inflow and outflow flow regulators. In some embodiments, the operating parameter may be assigned according to a time schedule of the control algorithm that corresponds to a heartbeat. Preferably, the ratio of fluidic inflow to fluidic outflow is adjustable to maintain a control condition within a control range.

The invention has been described herein in detail in order to comply with the patent statutes and to provide those skilled in the art with information needed to apply the novel principles of the present invention. However, it is to be understood that various modifications to the invention may be accomplished without departing from the scope of the invention.

The invention claimed is:

1. A method for controlling fluid flow in a human heart, the method comprising:

(a) establishing a model cutoff frequency of a system including a coronary target region, wherein the target region is considered a low-pass filter;

(b) controllably delivering an inflow pulse of fluidic inflow to the target region through a coronary vessel of the target region in an inflow volume within an inflow time period, wherein the fluid inflow has a therapeutic effect upon the target region;

(b) controlling an outflow pulse of fluidic outflow from the target region in an outflow volume within an outflow time period, wherein a net volume is defined by a difference of the inflow volume and the outflow volume; and wherein the fluidic inflow pulse and the fluidic outflow pulse are relatively controlled to an adjustable ratio of inflow time period to outflow time period, and wherein a total time period from onset of the fluidic inflow pulse to termination of the fluidic outflow pulse, including any delay therebetween, is greater than an interval of the cutoff frequency of the target region.

2. The method as in claim 1 wherein an onset of the fluidic inflow pulse and an onset of the fluidic outflow pulse are relatively controlled.

3. The method as in claim 2 wherein the onset of the fluidic inflow pulse and the onset of the fluidic outflow pulse are relatively controlled based on a physiological time period.

4. The method as in claim 3 wherein the physiological time period is a heartbeat, wherein the heartbeat is defined from a first systole onset to an immediately subsequent systole onset.

5. The method as in claim 4 wherein a flow cycle is defined by the onset of the fluidic inflow pulse to termination of the fluidic outflow pulse, wherein flow cycle duration is measured with respect to the heartbeat, and wherein a flow cycle frequency is determined as the heartbeat rate divided by the number of heartbeats in the flow cycle, the flow cycle frequency being less than the model cutoff frequency.

6. The method as in claim 4 wherein the inflow time period includes one or more consecutive diastole periods, and the outflow time period includes one or more consecutive systole periods.

7. The method as in claim 1 wherein the fluidic inflow pulse and the fluidic outflow pulse are controlled at fixed flow rates.

8. The method as in claim 1 wherein the model cutoff frequency is approximated to be proportional to an inverse of a product of a fluidic flow resistance of the target region and a compliance of the target region.

9. The method as in claim 1 wherein the model cutoff frequency of the target region is established by measuring a frequency response.

10. The method as in claim 1 wherein the model cutoff frequency of the target region is established by monitoring an actual outcome for therapy delivery for compliance with or deviation from an expected outcome.

11. The method as in claim 10 wherein the expected outcome includes a pressure or pressure range in the target region, and deviation in the actual outcome from the expected outcome indicates a controller action selected from adjusted inflow pulse duration, outflow pulse duration, inflow volumetric flow rate, and outflow volumetric flow rate.

12. The method as in claim 1, including controlling the inflow volume to be greater than a target region volume of the target region.

13. The method as in claim 1, including controllably adjusting the adjustable ratio based upon at least one of a pressure and a temperature of the target region.

14. The method as in claim 1, including controlling the inflow pulse and the outflow pulse with one or more of a valve and a pump.

15. The method as in claim 1, including controlling the adjustable ratio in two or more priority conditions, wherein a first priority condition prioritizes the therapeutic effect, and a second priority condition prioritizes maintaining at least one of a pressure and a temperature of the target region within a respective pressure range and temperature range.

16. The method as in claim 1, including intermittently causing a drain pulse of fluidic outflow from the target region to adjust a pressure of the target region to a target pressure.

* * * * *